United States Patent
Jago et al.

(10) Patent No.: US 6,629,929 B1
(45) Date of Patent: Oct. 7, 2003

(54) METHOD AND APPARATUS FOR AUTOMATICALLY SETTING THE TRANSMIT APERTURE AND APODIZATION OF AN ULTRASOUND TRANSDUCER ARRAY

(75) Inventors: James Jago, Seattle, WA (US); David Rust, Seattle, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/291,034

(22) Filed: Nov. 8, 2002

(51) Int. Cl.[7] .............................. A61B 8/00; A61B 10/00
(52) U.S. Cl. ...................... 600/447; 600/443; 73/625
(58) Field of Search .................................. 600/437, 443, 600/447, 440, 449, 438, 444, 445; 73/625, 620; 128/916

(56) References Cited

U.S. PATENT DOCUMENTS

| | | | | |
|---|---|---|---|---|
| 5,072,735 A | * | 12/1991 | Okazaki et al. | 600/443 |
| 5,301,674 A | * | 4/1994 | Erikson et al. | 600/447 |
| 5,379,642 A | * | 1/1995 | Reckwerdt et al. | 73/625 |
| 6,123,670 A | * | 9/2000 | Mo | 600/447 |
| 6,217,516 B1 | * | 4/2001 | Poland et al. | 600/437 |

* cited by examiner

Primary Examiner—Marvin M. Lateef
Assistant Examiner—Ruby Jain
(74) Attorney, Agent, or Firm—John Vodopia

(57) ABSTRACT

A process for setting a focus in a ultrasonic imaging system includes receiving a point of interest and range of interest by a user input. A system controller of the system sets a focus zone on the point of interest and adjusts the aperture and apodization for the range of interest. If the range of interest can not be covered by one focal zone, further focal zones are added.

29 Claims, 5 Drawing Sheets

METHOD AND APPARATUS FOR AUTOMATICALLY SETTING THE TRANSMIT APERTURE AND APODIZATION OF AN ULTRASOUND TRANSDUCER ARRAY

BACKGROUND OF THE INVENTION

1. Field of the Invention

The present invention relates to a method for automatically setting a transmit aperture and a transmit apodization of an ultrasound transducer array.

2. Description of the Prior Art

Ultrasonic imaging systems use sound waves having frequencies greater than the audible range and generally include sound waves having frequencies in excess of 15–20 kHz. These systems operate on the pulse-echo principle that is used in SONAR and radar. In general, ultrasonic pulses are transmitted toward a target and echoes of the transmitted pulses bounce back from the target. The received echoes used to determine an image of the target.

There are a number of modes in which an ultrasonic transducer operates. The basic modes are A-mode, B-mode, M-mode and 2D-mode. The A-mode is amplitude mode in which signals are displayed as spikes that are dependent on the amplitude of the returning sound energy. The B-mode is a brightness mode in which the signals are displayed as various points whose brightness depends on the amplitude of the returning sound energy. The M-mode is a motion mode in which the B-mode is applied and a recorder such as a strip chart recorder allows visualization of a structure as a function of depth and time. The 2D-mode is two-dimensional imaging mode where the B-Mode is spatially applied by sweeping the beam so that structures are seen as a function of depth and width.

Ultrasonic imaging systems may be used to observe internal organs, tissues and vessels of a patient using a variety of the above-described imaging modalities. For example, B-mode scanning may be used to image tissues by portraying the tissues in a gray scale in which the brightness of a region is a function of the intensity of the ultrasound returns from corresponding regions of the tissues. In addition, Doppler scanning may be used to show the velocity of moving sound reflectors, such as blood flowing through an artery or vein.

A diagnostic ultrasound imaging system 10 is shown in FIG. 1. The ultrasound imaging system 10 includes a scanhead 20 having a transducer face that is placed in contact with a target area containing tissues, organs, or blood vessels of interest. The images of the ultrasonic pulses may be focused at preselected depths. There are two different relevant types of focus: receive focus and transmit focus. As explained below, the scanhead 20 includes an array of transducer elements 24, each of which transforms a transmit signal into a component of an ultrasound beam and transforms an ultrasound reflection into a respective receive signal. These signals are coupled between the scanhead 20 and an imaging unit 30 through a cable 26. The imaging unit is shown mounted on a cart 34. The imaging system also includes a control panel 38 for allowing a user to interface with the system 10. A display monitor 40 having a viewing screen 44 is placed on an upper surface of the imaging unit 30.

During operation, the transducer elements 24 in the scanhead 20 collectively transmit a beam 50 of ultrasound energy as shown in FIG. 2. Respective electrical signals, typically at a frequency of 1–20 MHz, are applied to all or some of the transducer elements 24. The number of transducer elements 24 to which electrical signals are applied determines the size of the transmit aperture. The size of the aperture affects the size of the imaging field and resolution, as explained below. In practice, the phases of the electrical signals applied to the transducer elements 24 are adjusted so that the beam 50 is focused in a focal position 52. The depth of the focal position 52 beneath the transducer face is controlled by the magnitude of the differences in phase of the electrical signals applied to the transducer elements 24. The focal length (or depth of field), which corresponds to the effective length of the focal position 52, is determined by the size and gain of the transmit aperture, i.e., the number of transducer elements 24 used to form the beam 50. The focal position 52 should ideally be positioned where features of maximum interest are located so that these features will be in the best attainable focus. The focal position 52 is shown in FIG. 2 as being considerably "sharper" than is typical in practice when used with human tissue. The ultrasound from the individual transducer elements 24 is diffracted so that the effective length of the focal position 52 is actually more of an area where the beam is narrowed rather than a location where the beam converges at one point. It is also a common practice to transmit multiple focal positions or zones along a single line to extend this area where the beam is narrowed.

As previously mentioned, the transducer elements are also used to receive ultrasound reflections and generate corresponding electrical signals. As shown in FIG. 3, the phase and gain of the received signals are also adjusted to effectively generate a receive beam 56 that is focused to a focal position 58 corresponding to the phase differences between the signals coupled from the transducer elements 24. (In the interest of clarity in FIG. 3, beam components for only two transducer elements 24 are shown, although it will be understood that beam components would exist for all active transducer elements). The receive beam can also be "steered", i.e., offset from an axis that is perpendicular to the transducer face, by adjusting the phase differences between the signals coupled from the transducer elements 24. In practice, the phase differences between these signals are adjusted as a function of time delay from each ultrasound transmission so that the focal position 58 dynamically varies with depth from a relatively deep position 60 to a relatively shallow position 62 from where the ultrasound is reflected. As explained below, the disclosed invention relates to the locations of the focal position 52 for the transmit beam 50 rather than the locations of the focal position 58 for the receive beam 56.

SUMMARY OF THE INVENTION

It is an object of the present invention to provide a device and method for adaptive control of the focal zone or focal zones of an ultrasonic transducer array in response to user input defining a range of interest by automatically determining the depth range for each focal zone and the transmit apodization.

According to the present invention, the ultrasound system allows a user to control the focal zones or zones of a transducer array by inputting a point of interest and a range of interest. In a first embodiment, the system includes a first input parameter for the point of interest, a second input parameter for the top of the range of interest and a third input parameter for the bottom of the range of interest. A second embodiment assumes that the point of interest is always in the center of the range of interest and includes a range of interest control and a point of interest control. In the second embodiment, the range of interest control defines a total range (i.e., the distance between the top and bottom of the range). The system receives these control parameters and determines the actual focal zones required by the beamformer to achieve the desired control. For example, an algorithm may be used to select actual focal zones in response to the range of interest. The actual focal zones selected may optionally be shown to the user. Furthermore, the user may also alter the selected focal zones.

In a more detailed embodiment, other user preferences such as desired image quality and/or frame rate may be used to determine the number of zones to be used to fill the range of interest (i.e., zone spacing) and the size of the transmit apertures (which determines the depth of field for a single zone).

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings, wherein like reference characters denote similar elements throughout the several views.

DETAILED DESCRIPTION OF THE PRESENTLY PREFERRED EMBODIMENTS

Figure 1:
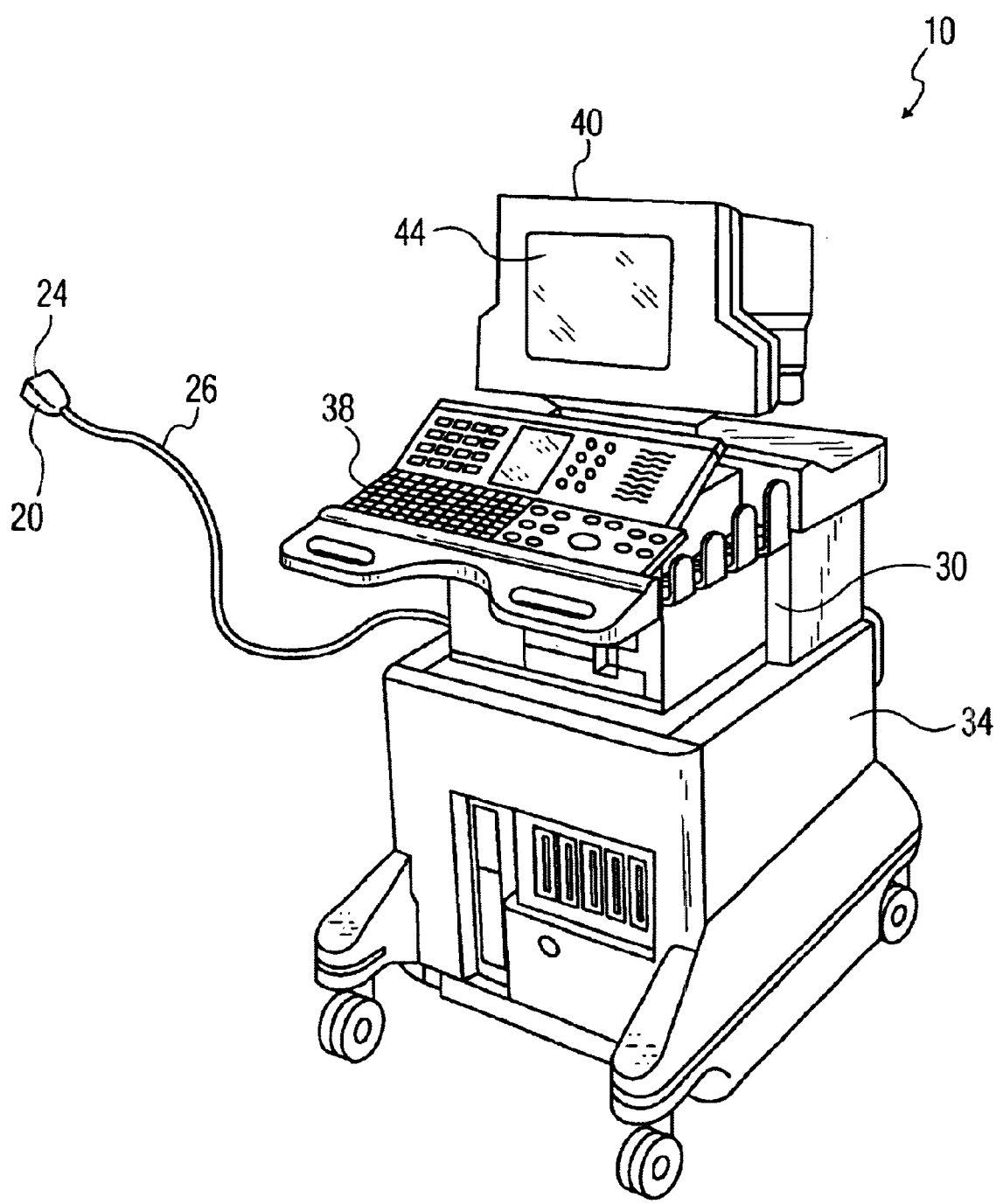
FIG. 1 is an isometric view of a diagnostic ultrasound imaging system.
Figure 2:
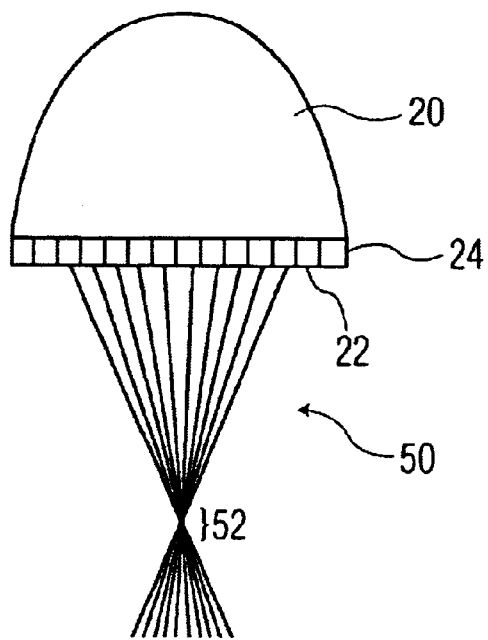
FIG. 2 is a schematic diagram of an ultrasound scan head of the system of FIG. 1 showing a transmit beam.
Figure 3:
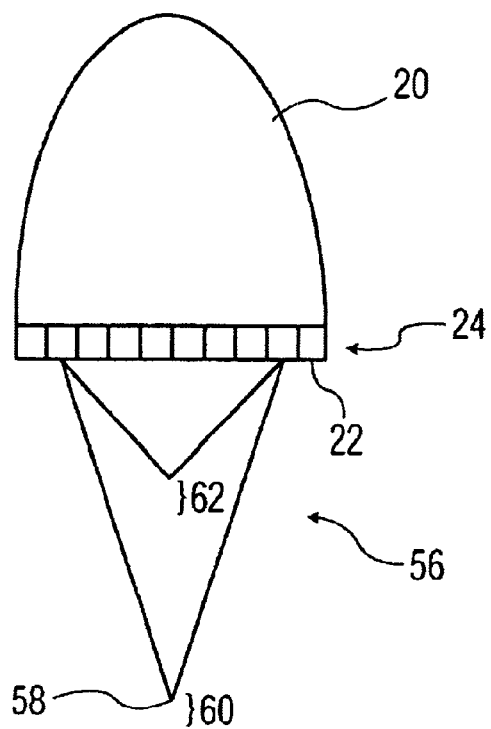
FIG. 3 is a schematic diagram of an ultrasound scan head of the system of FIG. 1 showing a received beam.
Figure 4:
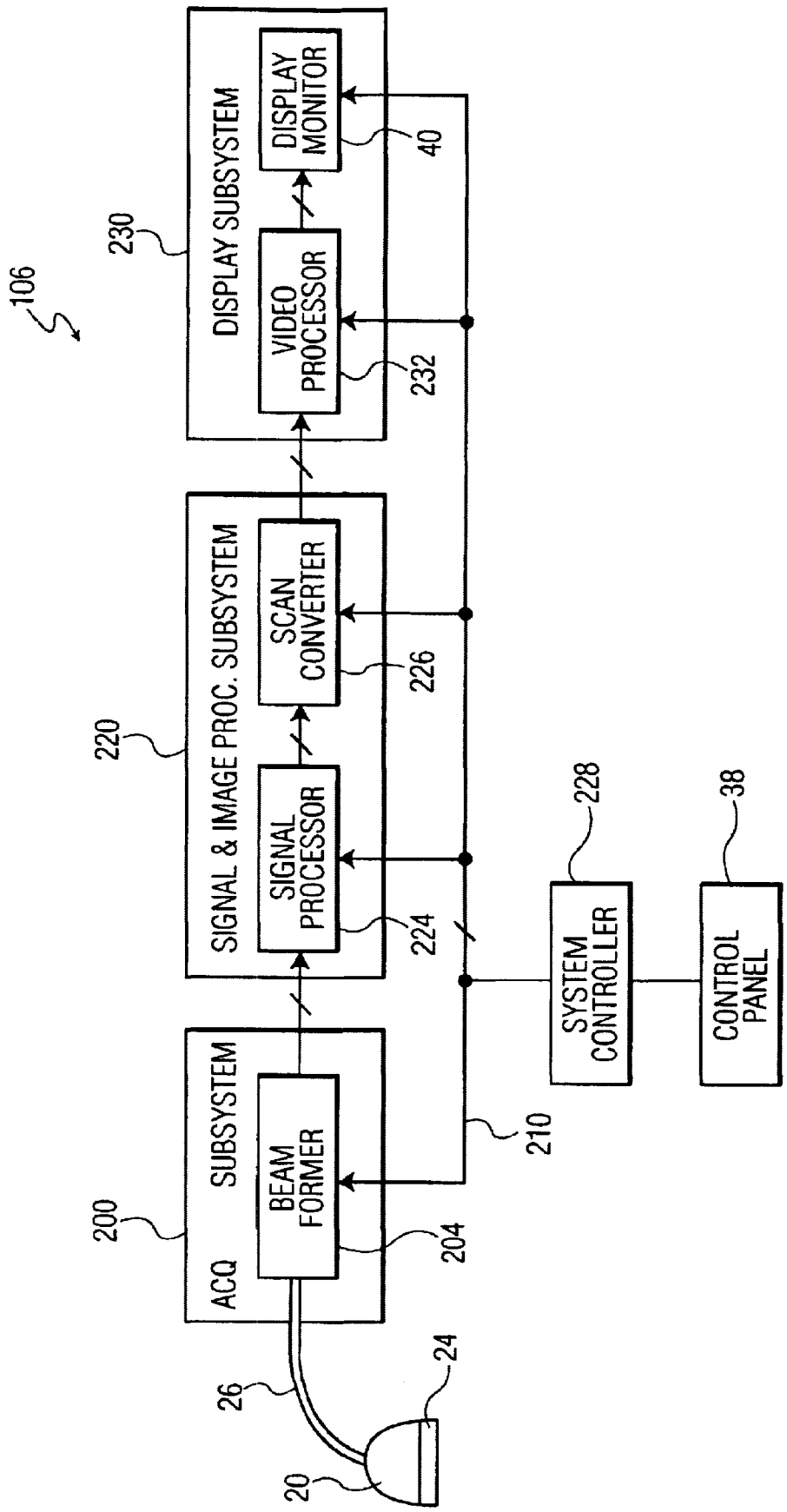
FIG. 4 is a block diagram of an embodiment of an imaging unit according to the present invention that may be used with the system of FIG. 1.

One embodiment of an ultrasound imaging system 10 according to the present invention is shown in FIG. 1. The system 10 differs from the prior art primarily in that the imaging unit 30 of system 10 is different. The components used in the imaging unit 30 according to the present invention are explained with reference to FIG. 4.

The imaging unit 30 according to the present invention includes an acquisition subsystem 200 that includes a beamformer 204 coupled to the scanhead 20 through the cable 26. Electric signals from the transducer elements 24 of scanhead 20 are applied to the beamformer 204, which processes the signals corresponding to echoes of each acquired scanline into a beam. As explained above, the beamformer 204 applies electrical signals to the transducer elements 26 in the scanhead 20 to cause the scanhead to transmit a beam of ultrasound energy. The beamformer 204 controls the respective delays of the signals applied to the transducer elements 24 of scanhead 20 to focus the transmit beam to a specific depth. The location of the focal position is controlled by control data applied through a control line 210 from a system controller 228.

The received signals from the beamformer 204 are applied to a signal and image processing subsystem 220, which includes a conventional processor 224 and a conventional scan converter 226. The signal processor receives the signals from the beamformer to generate image data corresponding to an image. The system controller 228 may apply appropriate control data to the beamformer 204 over control line 210 to control the location of the focal position or positions. The system controller 228 may also couple further data to the beamformer 204, such as data controlling the sizes of the transmit and receive apertures. The image data from the signal processors are then applied to the scan converter 226, which arranges the image data into respective ultrasonic image frame data of the desired image format.

The image frame data from the signal and image processing subsystem 220 are then transferred to a display subsystem 230, which includes a video processor 232 and a display monitor 40. The video processor 232 converts the image frame data from the scan converter 226 into appropriate video signals, such as National Television System Committee (NTSC) or Super Video Graphics Adapter (SVGA) video signals, for use by the display monitor 40.

Figure 5:
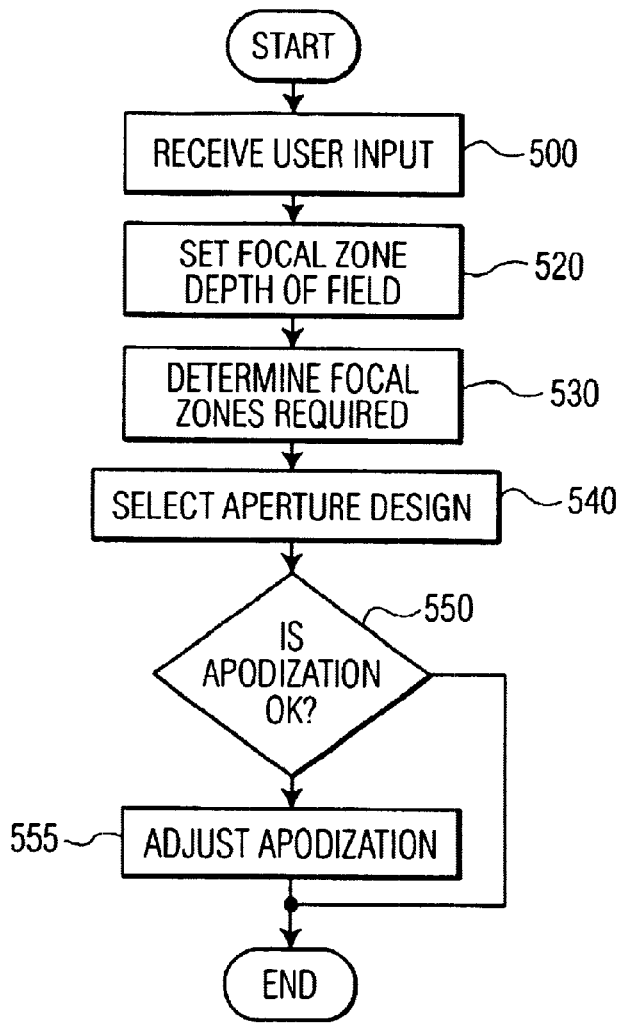
FIG. 5 is a flow diagram showing the steps of focusing control which may be used in the imaging unit of FIG. 4.

Referring to FIG. 5, a method for controlling a focusing operation in the imaging unit 106 begins when a user of the system 100 inputs a desired point of interest and a range of interest using control panel 38, step 500. The point of interest may be defined by a distance in a direction normal to the center of the transducer array. The range of interest may be defined as a length or distance covering a depth of a field of interest along a line normal to the center of the transducer array. The input of the point of interest and range of interest may be accomplished in many ways. The user may, for example, input one value for the point of interest, another value for the top of the range of interest and a third value for the bottom of the range of interest. Alternatively, the user may input a point of interest and a range of interest such that the system controller 228 assumes that the point of interest is in the center of the range of interest. In a specific embodiment, the control panel may include a switch which is pressed to switch between focus position control and focus range control. Turning the control adjusts the value of the selected one of these two parameters.

After receiving the data, the system controller 228 determines the optimum set of actual transmit focal zones to use. To make this determination, the system controller 228 first assigns a depth of field to each available focal zone of an aperture set of the transducer, step 520. Each aperture set is a set of focal zones which share certain characteristics, such as the number of scan lines supported, transmit apodization, and ratio of focal depth to aperture size. The various available aperture sets of the transducer are defined in the beamformer 204. The various available aperture sets may be defined as specific aperture sets saved in a memory and/or defined as a description used to form aperture sets on-the-fly for a specific use. The system controller 228 then determines how many sequential focal zones are required to cover the user selected focal range by stacking the depths of field of the focal zones and comparing to the user selected focal range, step 530. If more than one aperture set is available for use, steps 520 and 530 are performed for each of the multiple transmit aperture sets.

The system controller 228 then selects a transmit aperture design based on, for example, image quality (larger apertures and more transmit zones) and/or frame rate (smaller apertures and fewer transmit zones) considerations, step 540 (the selection of a transmit aperture design is discussed in more detail below). As a default setting, the system controller 228 selects the highest available image quality.

Figure 7A:
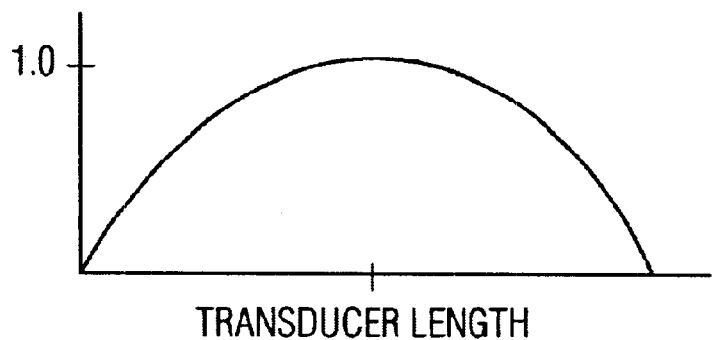
FIGS. 7a–7c each illustrate an apodization curve for the transducer array of the present invention.
Figure 7B:
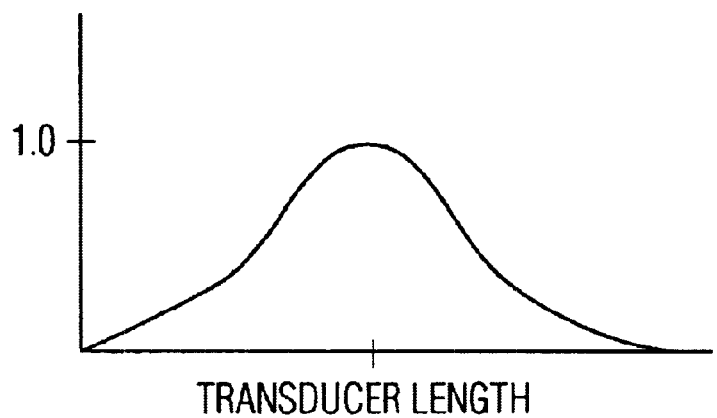
Figure 7C:
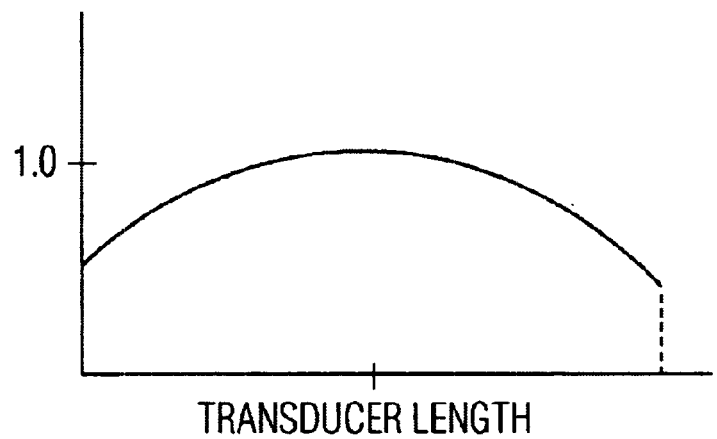

The system controller 228 then determines whether the apodization is appropriate for the depth of field of the selected focal zones, step 550, and adjusts the apodization if required, step 555. Apodization is the weighting of the drive signals to the different elements of the transducer array 24. More specifically, apodization is the weighting of the drive signals so that the amplitude of the ultrasound transmit signal degrades from the center to the sides of the transducer array. This variation in amplitude is illustrated in FIG. 7a. Apodization reduces acoustic noise generated by targets that are not along the beam direction. However, it also reduces lateral resolution, i.e., the ability to distinguish targets that are closely spaced laterally. Apodization also varies the depth of field of the focus. The degree of variation of the depth of field of the focus may be adjusted to suit a particular requirement of the system. Focal regions which are short in depth can be sharply focused with a weak apodization curve as shown in FIG. 7c while focal regions which are longer in depth are more gently focused over a great depth with a stronger apodization curve as shown in FIG. 7b.

The user may input further data to the control panel such as a preferred image quality and/or frame rate. According to this optional embodiment, the system controller 228 must take the image quality and frame rate parameters into consideration when selecting the transmit aperture design in step 530. Image quality is a function of the lateral resolution, which is itself determined by the beam width—the narrower the beam, the better the lateral resolution. The lateral beam width is defined by the following formula:

Lateral Beam Width=(Depth·Wavelength)/Aperture Size, where Depth is the distance from the array to the focal zone, Wavelength is the wavelength of the ultrasound signal, and Aperture Size is the width of the aperture of the transducer array. According to the formula, increasing the aperture will reduce the beam width and hence increase the image quality. However, changing the aperture size also affects the depth of field of the focal zone—the larger the aperture, the smaller the depth of field of the focal zone.

The frame rate relates to the time required to obtain an image in the range of interest or some other defined frame of reference. Each focal zone requires a separate ultrasound transmission beam and reception beam. Therefore, as the number of focal zones is increased, the frame rate of the image slows down because the amount of data required for each image frame increases.

In the following illustrative example, two aperture sets are available for a transducer. Aperture Set 1 includes 8 focal zones, each having a depth of field of 10 mm for an entire field depth of 80 mm. Aperture Set 2 includes 16 focal zones, each having a depth of field of 5 mm for covering the same entire field depth of 80 mm. Furthermore, the range of interest in this example is 25 mm. Accordingly, Aperture Set 1 requires 3 focal zones and Aperture Set 2 requires 5 focal zones to cover the range of interest. The algorithm for determining which Aperture Set of focal zones to use first selects the Aperture Set having the highest image quality, i.e., Aperture Set 2. If the frame rate is not a concern, the algorithm will select Aperture Set 2 automatically and the algorithm is complete. However, if the user has input a desired frame rate value or a preference for a high frame rate (for example, through a separate user control that sets a preference for high image quality, high frame rate, or a compromise of thereof), or if the system has a frame rate limitation, the algorithm determines whether the 5 focal zones of the set 2 required to cover the range of interest meet the frame rate limitation. If not, Aperture Set 1 which requires only 3 focal zones is used.

Instead of using user defined values for the frame rate parameter and the image quality parameter, the focusing procedure may use default values. Furthermore, instead of checking both parameters, the focusing procedure may use only the frame rate or image quality parameters.

Figure 6:
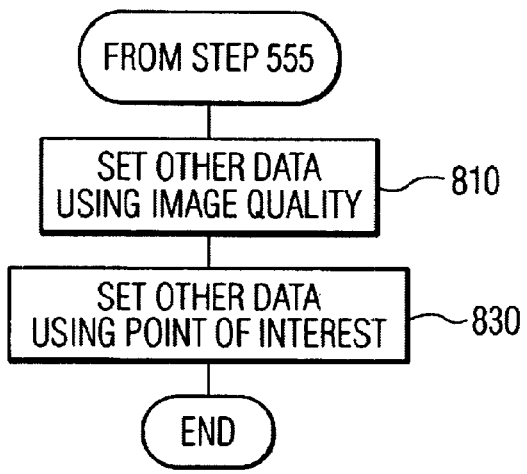
FIG. 6 is a partial flow diagram showing optional steps for setting additional parameters.

FIG. 6 shows further optional steps which may be performed with step 555. The frame rate and image quality parameters may be used in the determination of other parameters that affect image quality and temporal resolution (frame rate), step 810, such as transmit line density, receive line density, RF interpolation, pulse repetition frequency, synthetic aperture.

Furthermore, the user selected point of interest and range of interest may further be used to set other parameters, step 830, such as the default HD zoom box position and size and the default color box position and size.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A process for controlling the focus of a transmit beam of a transducer array in a scan head of an ultrasound imaging system, the ultrasound imaging system further comprising a beamformer, a signal processor, a display, and a system controller, wherein the system controller is connected to each of the scanhead, the beamformer, the signal processor, and the display, said process comprising the steps of:

receiving, by the system controller, user input including a point of interest and defining a range of interest above and below the point of interest, the point of interest defined as a normal distance from a center of the transducer array; and selecting, by the system controller, of focal zones for the transmit beam of the transducer array to be used for ultrasonic imaging of the point of interest and the range of interest input by the user from at least one aperture set of focal zones allowed by the beamformer.

2. The process of claim 1, further comprising the step of adjusting an apodization of the transducer array to attain a desired field of focus for each of the selected focal zones.

3. The process of claim 1, wherein said step of receiving user input includes receiving distance values representing a point of interest and a range of interest, and said process further comprises centering said range of interest about said point of interest.

4. The process of claim 1, wherein said step of receiving user input further includes receiving a top of a range of interest and a bottom of a range of interest, each comprising a normal distance from a center of the transducer array.

5. The process of claim 1, wherein said step of receiving further comprises receiving a minimum image quality parameter and said process further comprises the steps of determining, by the system controller, whether the image quality of each of the selected focal zones exceeds the minimum image quality parameter.

6. The process of claim 5, wherein said step of receiving further comprises receiving a frame rate parameter and said process further comprises the steps of determining, by the system controller, whether the frame rate parameter is met by the selected focal zones.

7. The process of claim 1, wherein said step of receiving further includes receiving a frame rate parameter and said process further comprises the steps of determining, by the system controller, whether the frame rate parameter is met by the selected focal zones.

8. The process of claim 1, further comprising the step of determining by the system controller the positions of the selected focal zones in the range of interest based on the location of the point of interest.

9. The process of claim 1, wherein the beamformer includes a plurality of aperture sets of focal zones for the scan head and transducer array, and said step of selecting the focal zones includes selecting one of the aperture sets of focal zones.

10. The process of claim 9, wherein the step of receiving further comprises receiving a user preference for a desired image quality and the process further comprises the step of selecting one of the aperture sets for use with the point of interest and the range of interest based on the desired image quality.

11. The process of claim 10, wherein the step of receiving further comprises receiving a user preference for a desired frame rate and the process further comprises the step of selecting one of the aperture sets for use with the point of interest and the range of interest based on the desired image quality and the desired frame rate.

12. The process of claim 9, wherein the step of receiving further comprises receiving a user preference for a desired frame rate and the process further comprises the step of selecting one of the aperture sets for use with the point of interest and the range of interest based on the desired frame rate.

13. The process of claim 11, further comprising the step of setting, by the system controller, at least one of transmit line density, receive line density, RF interpolation, pulse repetition frequency, and synthetic aperture in response to at least one of the desired frame rate and the desired image quality.

14. The process of claim 1, further comprising the step of setting, by the system controller, the size and position of one of a default HD zoom box and a color box in response to the range of interest and the point of interest.

15. An ultrasound imaging system, comprising:
   an imaging unit including a scan head and a transducer array for producing a transmit beam for ultrasonic imaging;
   an input device;
   a display;
   a beamformer including at least one aperture set of focal zones,
   a signal processor,
   a system controller for receiving data by a user through said input device, the data including a point of interest and defining a range of interest above and below the point of interest, the point of interest defined as a normal distance from a center of the transducer array, said system controller connected to each of said imaging unit, said display, said signal processor, and said beamformer, said system controller including means for selecting focal zones for the transmit beam of said transducer array to be used for ultrasonic imaging of the user defined point of interest and range of interest from the at least one aperture set of focal zones in said beamformer.

16. The system of claim 15, said system controller and beamformer further comprising means for adjusting an apodization of said transducer array.

17. The system of claim 15, wherein said system controller receives a user defined point of interest and a range of interest centered about said point of interest.

18. The system of claim 17, wherein said system controller includes a control switch for switching between range of interest control and point of focus control and input means for inputting, by the user, a desired value for the selected one of the range of interest control and the point of interest control.

19. The system of claim 15, wherein said system controller includes means for receiving the point of interest, a top of a range of interest and a bottom of a range of interest, each being defined by a normal distance from the transducer array.

20. The system of claim 15, wherein said system controller further comprises means for receiving a minimum image quality parameter and means for determining whether the image quality of each of the selected focal zones exceeds the minimum image quality parameter.

21. The system of claim 20, wherein said system controller further comprises means for receiving a frame rate parameter and means for determining whether the frame rate parameter is met by the selected focal zones.

22. The system of claim 15, wherein said system controller further comprises means for receiving a frame rate parameter and said system controller further comprises means for determining whether the frame rate parameter is met by the selected focal zones.

23. The system of claim 15, wherein said system controller further comprises means for positioning the selected focal zones in the range of interest based on the location of the point of interest.

24. The system of claim 15, wherein said means for determining focal zones comprises means for setting a depth of field for each of the available aperture sets of focal zones, means for determining the number of focal zones required to cover the range of interest defined by the user input data for each of the aperture sets of focal zones, and means for selecting the required focal zones from one of the aperture sets.

25. The system of claim 24, wherein the user input data received by said controller further comprises a user preference for a desired image quality and said system controller further comprises means for selecting one of the available aperture sets for use with the point of interest and the range of interest based on the desired image quality.

26. The system of claim 25, wherein the user input data received by said system controller further comprises a user preference for a desired frame rate and said system controller further comprises means for selecting one of the available aperture sets for use with the point of interest and the range of interest based on the desired image quality and the desired frame rate.

27. The system of claim 24, wherein the user input data received by said system controller during the step of receiving further comprises a user preference for a desired frame rate and system controller further comprises means for selecting one of the available aperture sets for use with the point of interest and the range of interest based on the desired frame rate.

28. The system of claim 27, wherein said system controller further comprises means for setting at least one of transmit line density, receive line density, RF interpolation, pulse repetition frequency, and synthetic aperture in response to at least one of the desired frame rate and the desired image quality.

29. The system of claim 15, wherein said system controller further comprises means for setting the size and position of one of a default HD zoom box and a color box in response to the range of interest and the point of interest.

\* \* \* \* \*